United States Patent [19]

Weyrauch et al.

[11] Patent Number: 5,420,408

[45] Date of Patent: * May 30, 1995

[54] REAGENT BOTTLE IDENTIFICATION METHOD

[75] Inventors: Bruce Weyrauch, Newman Lake; Norman Kelln, Spokane; Leon Schmidt, Spokane; Charles Butts, Spokane; James Clark, Spokane; Kelsey Loughlin, Spokane; Gary Richardson, Mica, all of Wash.

[73] Assignee: Schiapparelli Biosystems, Inc., Fairfield, N.J.

[*] Notice: The portion of the term of this patent subsequent to Oct. 18, 2011 has been disclaimed.

[21] Appl. No.: 241,469

[22] Filed: May 12, 1994

Related U.S. Application Data

[62] Division of Ser. No. 916,221, Jul. 16, 1992, Pat. No. 5,357,095.

[51] Int. Cl.$^6$ .............................................. G06K 7/10
[52] U.S. Cl. ................................................... 235/454
[58] Field of Search .................. 235/454, 456; 382/68, 382/23

[56] References Cited

U.S. PATENT DOCUMENTS 4,760,247  7/1988  Keane et al. ........................ 235/456

Primary Examiner—Donald Hajec
Assistant Examiner—Edward Sikorski
Attorney, Agent, or Firm—Wells, St. John, Roberts, Gregory & Matkin

[57] ABSTRACT

An automatic chemical analyzer utilizes reagents supplied in reagent bottles. The reagent bottles are labeled on their bottom surfaces with an identification label bearing a machine-readable identification code. The automatic chemical analyzer includes a reagent tray having a plurality of tray apertures therein which receive coded reagent bottles and which expose the bottom surface of each bottle for optical viewing of the machine-readable identification code. The analyzer further includes optical scanner means positioned below the reagent tray for reading the machine-readable identification code on the bottom surfaces of reagent bottles within the tray apertures. The tray apertures are selectively located over the optical scanner means so that the analyzer can identify the reagent bottle and the contents thereof.

The identification label has a spaced pair of position reference dots defining and orienting a label area. A plurality of bit fields surround the position reference dots, their positions being defined by the position reference dots. Each bit field maps to a single bit of a multi-bit binary bottle identification code. Bit dots are printed in selected bit fields to define the binary value of each bit of the multi-bit binary identification code.

10 Claims, 10 Drawing Sheets

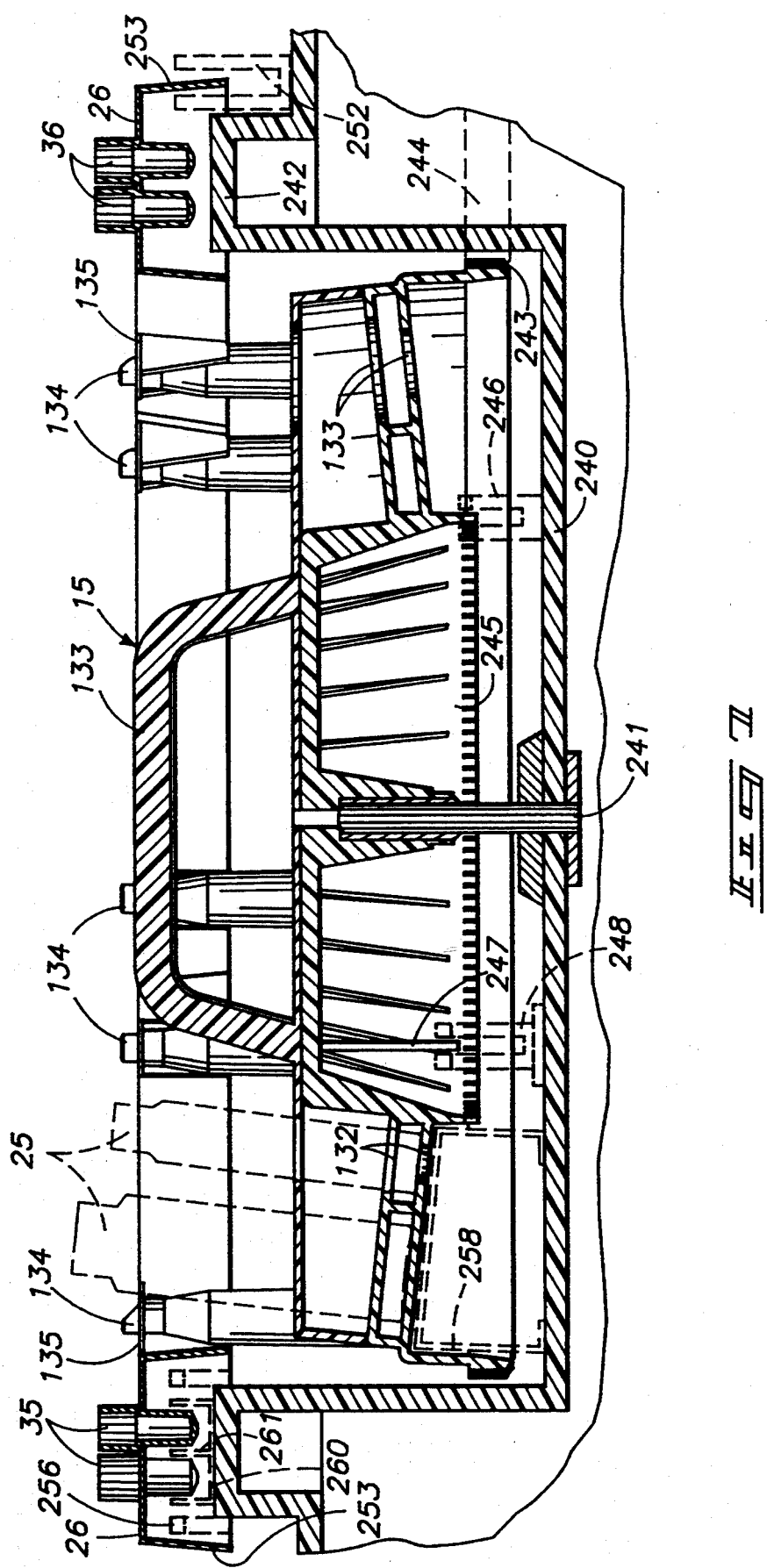

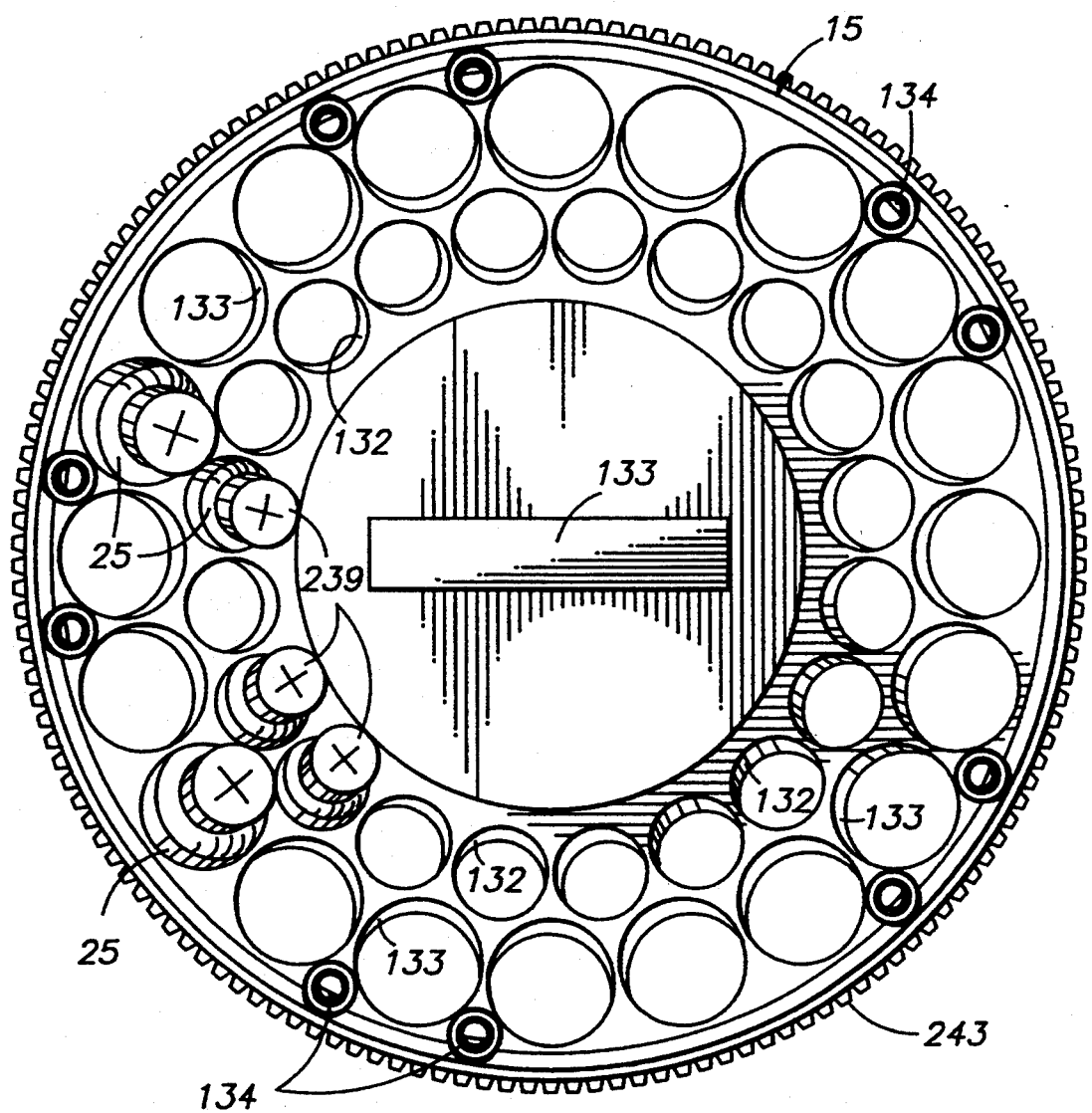
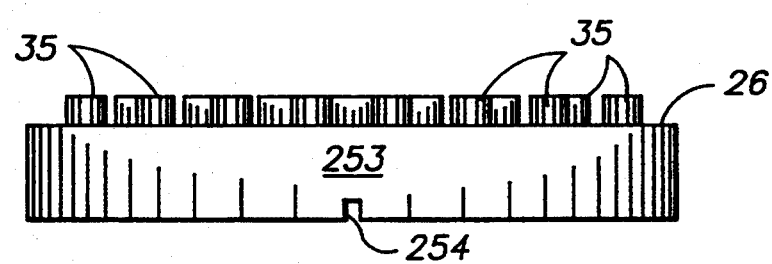

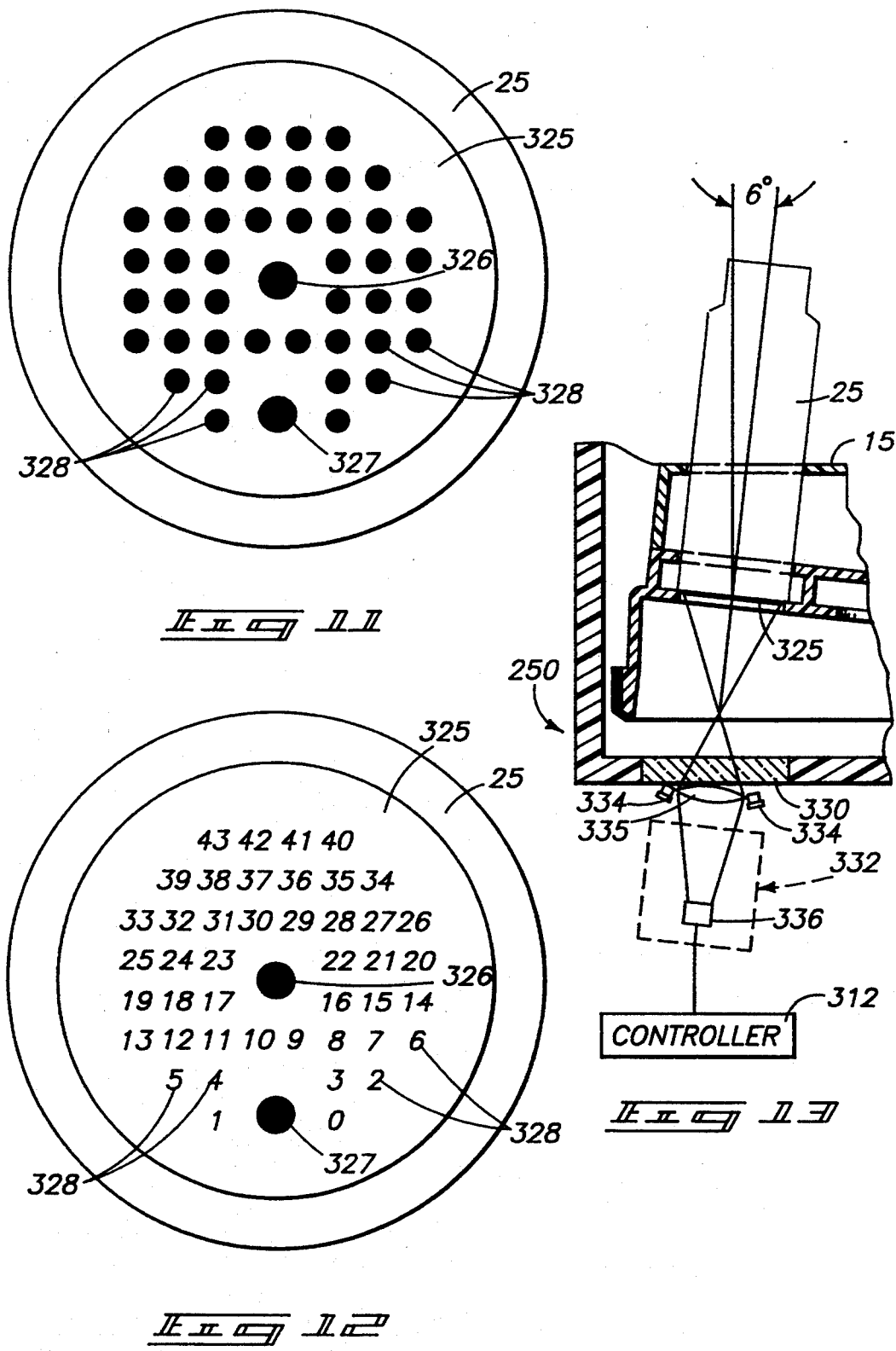

REAGENT BOTTLE IDENTIFICATION METHOD

This application is a division of application Ser. No. 07/916,221, filed on Jul. 16, 1992, now U.S. Pat. No. 5,357,095, issued on Nov. 18, 1994.

TECHNICAL FIELD disclosure pertains to a clinical chemistry analyzer for testing of patient samples, such as blood or urine. It generally relates to automatic chemical analyzers for directly measuring properties of reacted liquids by photometric systems. It specifically pertains to an identification system for regent bottles used in conjunction with the testing instrument, including machine-readable labels affixed to the bottles.

BACKGROUND OF THE INVENTION

Automated analyzers have been developed for biochemical analysis of patient samples, such as whole blood, serum, urine, plasma and cerebral spinal fluid. Most such equipment available today is complicated to operate, large in size and high in cost.

The operation of such equipment is technically complicated. It typically requires specialized operators to be available at all times, with commensurate personnel expenses being encountered. It is usually designed for use by large laboratories serving a wide geographic area or by a large medical facility. These existing analyzers carry out tests in a defined sequence of operations designed for efficient, high volume usage.

Such large scale capacity is not always required, particularly in smaller medical clinics where large volumes of blood samples are not encountered on a daily basis. The present chemical analyzer was developed to meet the practical needs of smaller medical settings. It is designed as a desk-top unit that can be operated without specialized laboratory training. Its throughput is adequate for meeting typical clinical applications. As an example, it can be designed to produce a maximum of 164 test results per hour for routine, single reagent chemistries. To provide a representative wide number of reagents, the analyzer has been designed to have a capacity of 40 reagent containers of two different sizes on board. Its capacity can be effectively doubled by utilizing two of the chemistry instruments in tandem, both being controlled by a common workstation.

The compact nature of the analyzer can be partially attributed to the fact that a single probe arm and pipette service all of the functional liquid-handling components included within it. The common pipette is used for transferring samples and reagents, as well as for diluting liquids as needed by particular test requirements.

To obtain large volumes of tests, conventional laboratory analyzers are programmed to conduct test procedures in a fixed sequence of events. While predetermined test sequences are practical in high volume chemical analyzer applications, there is a need for more flexible operation when scaling such test procedures to meet the needs of smaller medical facilities.

The present invention provides testing flexibility by permitting random access to each cuvette on a test turntable and to each container (cups, wells and reagent bottles) on a sample/reagent tray. It is therefore not necessary for the instrument to sequence through any predetermined processing steps—the controlling software can tailor the required steps to the tests currently requisitioned. This permits a greater number of tests to be conducted while using a minimum number of containers, cuvettes and reagent bottles. The software controls the sequencing of tests based upon predetermined priority schedules, rather than defined test sequences dictated by the nature of the tests being conducted.

The automated controls for the present chemical analyzer minimize operator training and required skill levels. Reagent bottles are automatically read and identified by applied computer coded labels. Sample and reagent sensing that occurs automatically during operation of the analyzer notifies the operator of depleted liquid conditions as they occur.

Further details concerning the system will be evident from the following description.

BRIEF DESCRIPTION OF THE DRAWINGS

The preferred embodiment of the invention is illustrated in the accompanying drawings, in which:

FIG. 7 is a sectional view taken along line 7—7 in FIG. 6;

FIG. 8 is a plan view of the reagent tray;

FIG. 9 is a side elevation view of a cup segment removed from the tray;

FIG. 11 is a bottom view of a labelled bottle;

FIG. 12 is a similar view, showing the label encoding pattern; and

FIG. 13 is a diagrammatic view of the label reading equipment in a chemical instrument.

DETAILED DESCRIPTION OF THE PREFERRED EMBODIMENT

Figure 1:
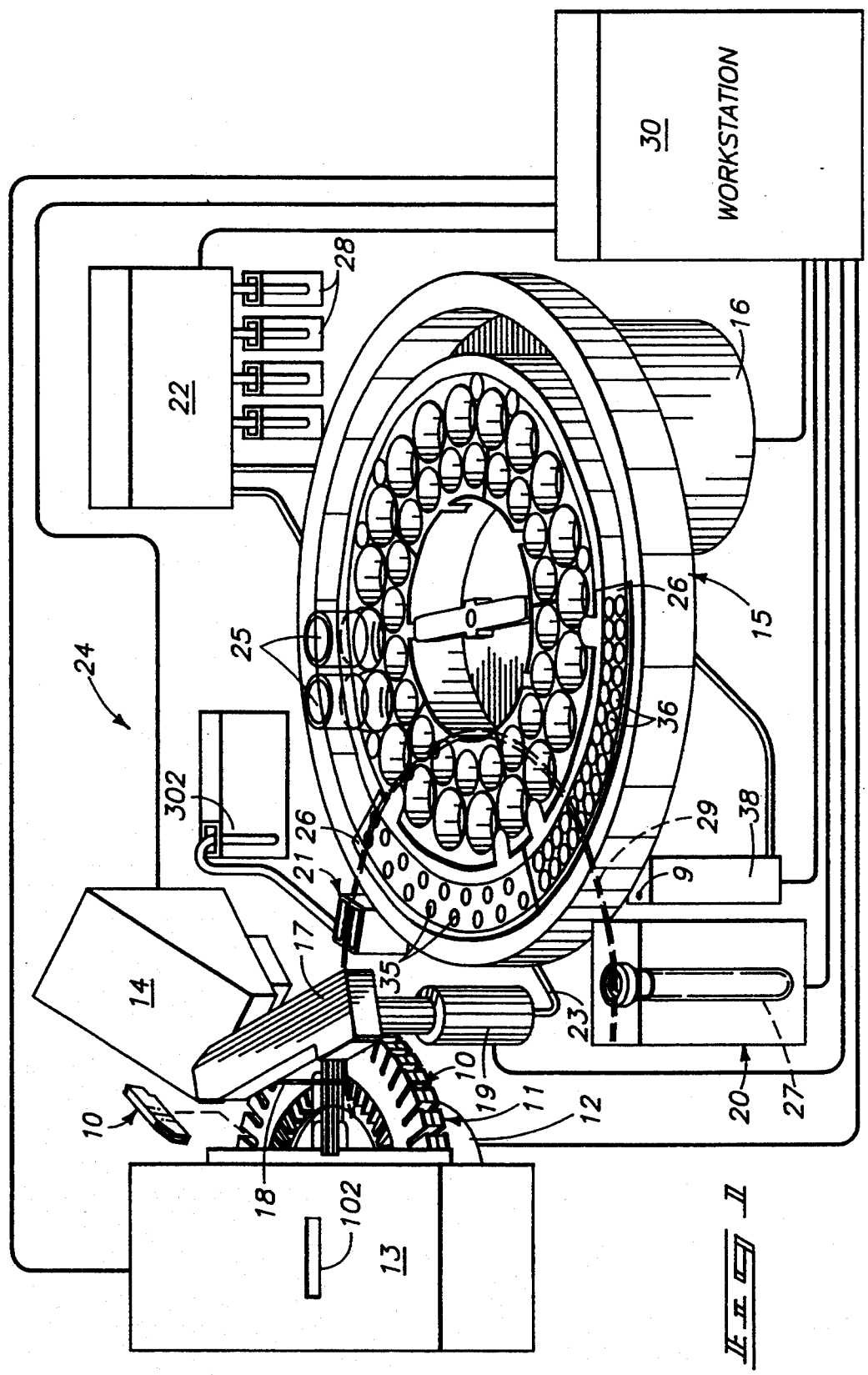
FIG. 1 is a diagrammatic perspective view of the principal components in the analyzer.

This disclosure of the invention is submitted in furtherance of the constitutional purposes of the U.S. Patent Laws "to promote the progress of science and useful arts" (Article 1, Section 8).

System Overview

The automatic chemical analyzer (generally illustrated in FIGS. 1-3) includes a turntable 11 rotatably mounted about a first vertical axis. A plurality of disposable cuvettes 10 are releasably mounted to the turntable 11. A first power means, shown as motor 12, is operably connected to turntable 11 for alternately (1) indexing it at a stationary angular position about the first axis with a selected cuvette 10 positioned at a cuvette access station A or (2) turning it about the first axis while mixing or centrifuging contents of cuvettes mounted to it.

First analytical means, illustrated as an optical system 14, is provided adjacent to the turntable 11 for performing tests on the contents of the cuvettes 10 as they rotate about the turntable axis.

A tray 15 is rotatably mounted about a second vertical axis parallel to and spaced from the first axis. A plurality of containers 25, 35, and 36 are positioned about tray 15 for reception of samples and reagent liquids. Second power means, illustrated as motor 16, is operably connected to the tray 15. The motor 16 indexes tray 15 to a stationary angular position about the second axis with a selected container positioned at a container access station C.

The analyzer also includes a probe arm 17 movable about a third vertical axis parallel to the first axis. Probe arm 17 supports a downwardly-extending open pipette 18. The vertical pipette 18 is movable along an arcuate path centered about the third axis and intersecting both the cuvette access station A and container access station C. It can move along the arcuate path in a random fashion to transfer liquid from a container positioned on the tray at the container access station C to a cuvette 10 positioned on the turntable 11 at the cuvette access station A. The arcuate path of the pipette 18 can be visualized along a protective groove 29 formed at the exterior of the enclosure 39 housing the chemistry instrument 24.

The illustrated embodiment of the clinical chemistry analyzer consists of two major components: a chemistry instrument 24 and a workstation 30. The chemical instrument accepts liquid patient samples for testing purposes, performs appropriate optical and/or potentiometric measurements on the samples, and communicates the resulting test data to workstation 30. Workstation 30 is used by the operator to enter data, control operation of instrument components, accept data generated by the instrument, manage and maintain system information, and generate visual and printed reports about assays and instrument performance.

The chemistry instrument 24 is a separate unit with minimal operator controls. Either one or two identical chemistry instruments 24 can be linked to a single workstation 30, as required in a particular setting. The chemistry instrument 24 can perform several types of analysis. These include routine chemistries, electrolytes, therapeutic drug monitoring, drugs of abuse in urine, and other specialized tests.

The liquid-handling components that make up the chemistry instrument 24 are housed within enclosure 39 (FIGS. 2–5). It separates along a peripheral parting line 37 defining a lower supporting base 33 and an upper hinged cover 34.

The principal modular components of the chemistry instrument 24 are diagrammatically illustrated in FIG. 1. The illustrated components are specifically designed for use in association with a specially designed liquid cuvette 10.

A computerized operator interface to the chemistry instrument 24 is provided through connections to the programmable workstation 30. Most of the operator interactions with the analyzer take place at workstation 30. It is an external desktop computer located near the chemistry instrument(s) 24. It uses an industry standard operating system and bus structure, plus a hard disk. It is also provided with a custom instrument interface board for each associated chemistry instrument.

Operations required for sample testing of cuvette contents are not carried out in any predetermined sequence dictated by insertion of a sample into the chemistry instrument 24. Instead, workstation 30 serves as random access control means operably connected to the turntable 11, tray 15 and probe arm 17 for selectively transferring liquid from any container on the tray 15 to any cuvette 10 on the turntable 11 according to defined logical priority rules programmed into the workstation.

Operations carried out within the chemistry instrument 24 are timed about a repetitious cycle of operations. Each cycle involves sequentially transferring liquids to an awaiting cuvette 10 on the turntable 11, mixing the liquids, and centrifuging them for test purposes.

A monitor 31 is included within workstation 30 to display data, messages and optional menus for the operator. A keyboard 32 is included for operator input of data and instructions. A printer (not shown) of conventional design can also be provided in the system to record tests results and reports as required.

A plurality of test cuvettes 10 are releasably located within a motor-controlled turntable 11. It is powered by a DC motor 12. Motor 12 can be accurately controlled to (1) selectively index turntable 11 at a chosen angular position about its vertical axis for access to a particular cuvette and/or insertion of new cuvettes or (2) intermittently or reversibly rotate turntable 11 about its axis for mixing the contents of the cuvettes or (3) spin turntable 11 for centrifuging the contents of the cuvettes during photometric analysis.

A liquid transfer module includes a single probe arm 17 movably supported on the instrument 24 about a vertical axis. The outer end of probe arm 17 carries a downwardly extending pipette 18. Pipette 18 is used for transferring liquids between various locations about the chemistry instrument. Its lower or outer end is open for receiving or discharging liquids.

Probe arm 17 is supported and powered by a positioning assembly 19. The positioning assembly 19 has two stepper motors—one for imparting rotational motion to probe arm 17 and one for imparting vertical motion to it. Positioning assembly 19 can selectively move probe arm 17 and pipette 18 both angularly and axially relative to the vertical axis of probe arm 17.

The tip or lower end of pipette 18, while in an elevated condition permitting angular movement about the chemistry instrument 24, projects slightly into an open arcuate groove 29 (FIGS. 2, 3) formed about the cover 34 of the instrument enclosure.

Groove 29 is centered about the axis of probe arm 17 and is recessed within cover 34. It overlaps the bottom of pipette 18 to prevent its accidental engagement with the hands of an operator as the pipette travels from one station to the next. The protective overlap of the pipette tip eliminates the danger of accidentally impaling adjacent personnel when pipette 18 is subsequently lowered.

A cuvette dispenser module 13 is arranged on the framework of the equipment in a position immediately above the turntable 11. It includes a storage magazine for a plurality of stacks of cuvettes 10. It also includes an apparatus for transferring individual cuvettes 10 from a randomly selectable stack within the magazine 75 to a receiving compartment on turntable 11. Used cuvettes 10 are discarded into a removable cuvette disposal container (not shown) as new cuvettes are delivered to the turntable 11 by operation of a reciprocating ram. The cuvette disposal container can be a bag or bin into which used cuvettes drop when ejected from turntable 11.

The optical system 14 is contained within a housing positioned next to turntable 11. Optical system 14 performs photometric tests on the contents of cuvettes 10 while they are being spun about the turntable axis. The optical system 14 measures both fluorescent emissions and light absorbance by cuvette contents within the turntable 11. Photometric test groups typically supported include routine chemistries, special proteins, therapeutic drugs, and drugs of abuse.

For absorbency tests, the optical system 14 measures radiation at 180 degrees to the incident light. Readings are made at several wavelengths on a diode array, but only those points requested in specified test parameters are processed by the instrument 24. System offsets are subtracted from the results and the sample signal is divided by a reference signal. The negative logarithm of this ratio is the absorbance.

When conducting fluorescent tests, emitted radiation at a wavelength longer than that of the source is measured at 90 degrees to the incident beam. System offsets are subtracted and the intensity is then normalized using a reference signal.

A sample/reagent tray 15 is rotatably mounted about a vertical axis parallel to and spaced from the axis of turntable 11. It is rotatably powered by a stepper motor 16. Tray 15 consists of a circular reagent bottle support surrounded by separate interlocking ring segments 26. The removable ring segments 26 are used to hold reagents and samples required for assay procedures during operation of chemistry instrument 24.

Tray 15 supports a plurality of liquid containers, namely the reagent bottles 25, open cups 35 and open wells 36. The interchangeable ring segments 26 have two alternate configurations. One includes apertures for removably supporting individual sample cups 35. The other includes a plurality of integrally molded sample wells 36.

The individually removable cups 35 serve as containers for test samples supplied to the instrument 24 by the operator within one or more cups within a ring segment 26. Wells 36 are used by the instrument components in conjunction with operation of probe arm 17 for aliquoting of samples from a draw tube and for sample dilution purposes. The probe arm 17 can selectively transfer liquids from one well 36 to a second well 36, from a cup 35 to a well 36, or from a reagent bottle 25 to a well 36.

Access to the sample/reagent tray 15 is provided by a hinged tray access cover 8 formed in the enclosure cover 34. More limited manual access to a single ring segment 26 located at the front of the chemistry instrument 24 is provided by a hinged segment access port 7, which is a sub-assembly of cover 8.

Figure 3:
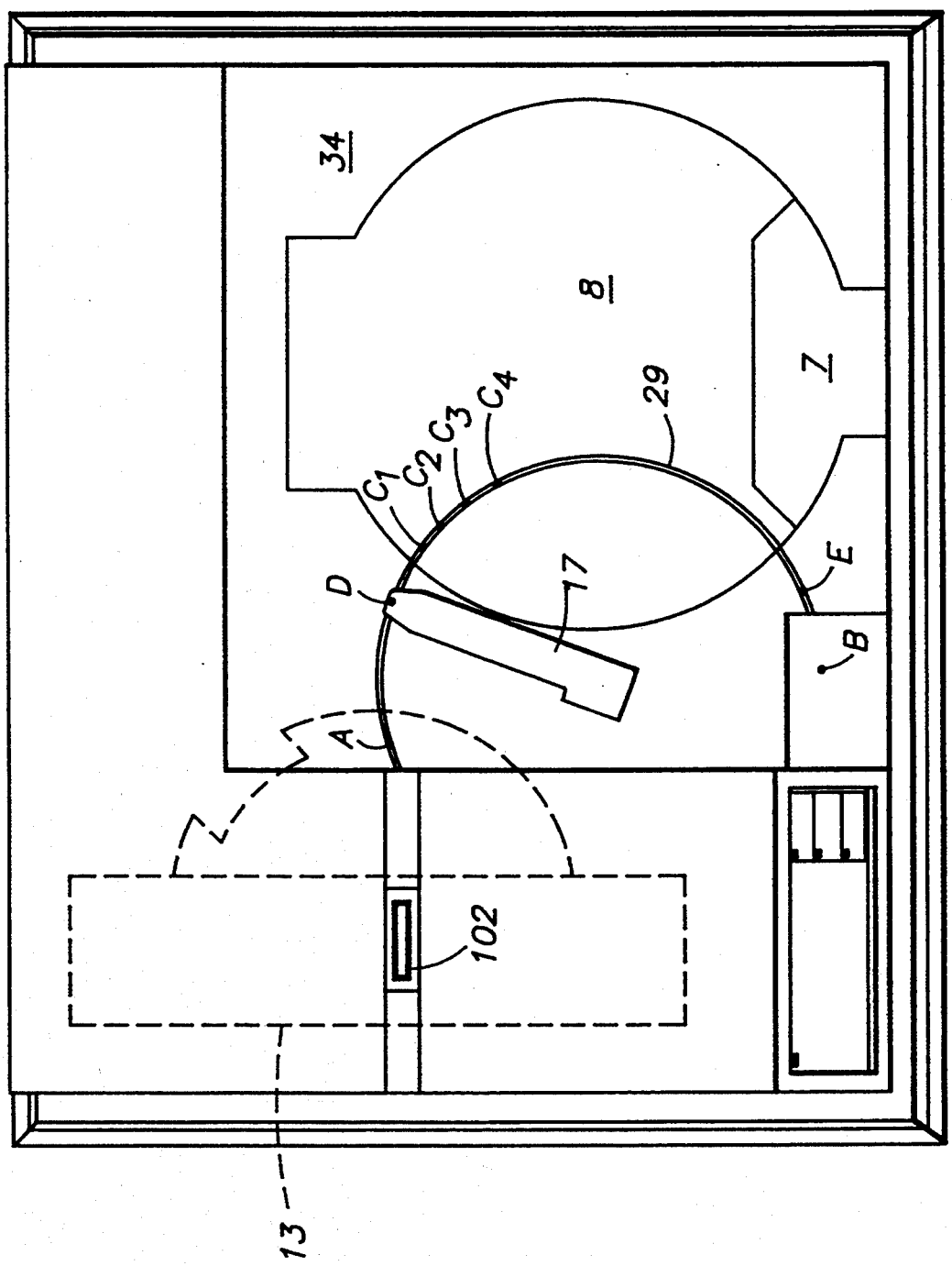
FIG. 3 is a plan view of the chemical instrument enclosure.

A stepper motor 16 can be operated to index sample/reagent tray 15 to a selected position about its axis with one or more selected containers at one of four container access stations shown in FIG. 3 at locations $C_1$, $C_2$, $C_3$, $C_4$ on the equipment framework. Each container access station intersects the path of pipette 18, which is coincident with groove 29.

Scanning means is provided next to the tray 15 for capturing identifying information from encoded indicia on a container positioned on it.

A cooling system (not shown) for the chemistry instrument 24 incorporates multiple thermoelectric cooling units. These are needed in the areas of the sample/reagent tray 15 and the turntable 11. Heat can be removed from the system by air exchange through a plurality of heat sinks.

A sample tube entry port 20 is provided on the framework for receiving and supporting successive individual draw tubes 27 as they are introduced into the instrument by the operator. Its primary use is to permit the taking of aliquots from positively identified, sealed patient draw tubes. It can also be used for delivery of control liquids from tubes of a similar exterior configuration, whether covered or open. Positive identification can be provided by an encoded label on each draw tube 27.

The label is scanned by a bar code reader included within the sample tube entry port 20.

Each draw tube 27, of conventional design, is sealed by a closure at its upper end. Sample tube entry port 20 supports each manually inserted draw tube 27 while pipette 18 pierces the closure 162 to access liquid sample material from the tube interior. Liquid removal from successive tubes 27 occurs at a sample access station B along the arcuate path 29.

Puncturing means are provided within the sample tube entry port 20 for temporarily forming an opening through a closure on a manually-delivered draw tube 27 placed within it. A ram positioned below the puncturing means receives and coaxially orients a manually placed draw tube 27 relative to the puncturing means. It moves the draw tube parallel to a fourth vertical axis (centered along the puncturing means) between a lowered position wherein the draw tube 27 is clear of the puncturing means and a raised position wherein the puncturing means forms a temporary opening through the draw tube closure for subsequent coaxial insertion of the pipette 18. The interior of the draw tube 27 is then accessible by subsequently inserting pipette 18 coaxially through the puncturing means.

A wash/alignment module 21 is located at a fixed position on the framework. Its first purpose is to provide vertical basins within which the lower end surfaces of pipette 18 can be flushed clean during or after liquid transfer cycles. It also supports a conductive sensing plate that verifies both the radial alignment and elevational position of pipette 18 about the pipette axis on the probe arm 17 for monitoring alignment of the pipette. These operations occur at a wash/alignment station D along the arcuate path 29 of pipette 18.

A capacitive sensing circuit is operably connected to the pipette 18 and to conductive members located next to the tray 15 and within the sample tube entry port 20. The sensing circuit detects the level of liquid in a container on the tray or a draw tube 27 as it is approached by the pipette.

A second analytical means, shown as an Ion Specific Electrode (ISE) module 38 of conventional design and operation, is included within the chemistry instrument 24. It is illustrated generally in FIG. 1. Potentiometric tests may be requested and run by the ISE module 38 simultaneously with photometric tests being conducted by the optical system 14.

Samples are delivered to the ISE module 38 by pipette 18 at a sample delivery station E along the arcuate path 29 (FIG. 3). Module 38 can include tests for the presence of a variety of analytes, such as sodium, potassium, chloride, lithium or calcium. For each analyte, all sample types are analyzed in the same manner. The different sample types can be loaded using different dilution factors.

The ISE module 38 consists of electrodes specific to the chosen analyte, a reference electrode and the associated fluid system required to process tested samples. The potentiometric measurement consists of a voltage difference between the analyte's electrode and the reference electrode.

Water is supplied to pipette 18 from a syringe module 22 connected to a water supply container in a container rack 28. The syringe module 22 consists of a volume displacement syringe and associated valves leading to a source of water and a waste water container (not shown). It is used for all aspirations of samples, reagents and diluents in the chemistry instrument 24. The syringe module is of conventional design.

Tubing 23 (FIG. 1) connects syringe module 22 to pipette 18. Tubing 23 contains water that can be moved in opposite directions to receive or discharge liquids at the lower end of pipette 18.

The above components are individually operable under control of a distributed computerized controller system governed by the programmable workstation 30. Workstation 30 is electronically linked to the instrument via a bi-directional communications interface. This interface is used to communicate patient requisitions to the chemistry instrument 24 and to receive the associated test results from the instrument 24. All control functions can be randomly initiated under control of scheduling software and logic to match pending requisition requirements and current instrument status conditions.

The external computer can send patient requisitions to the workstation either individually or in ring segment groups. The workstation can send test results to the external computer.

The control system associated with chemistry instrument 24 includes several dedicated microprocessors and programmable memory devices. They individually operate the system components as prioritized by scheduling software residing in the instrument CPU board. The workstation 30 includes monitoring means for maintaining a current record of the amount of liquid in containers on the sample/reagent tray 15. Controlling software associated with the microprocessors causes the mechanical components of the chemistry instrument 24 to carry out all operations efficiently and effectively without operator intervention, using a random sequence of movements dictated by outstanding test requirements.

The arrangement of operational stations along the arcuate path of pipette 18 permits transfer of liquids from a draw tube 27 at the sample access station B to a well 36 at a container access station $C_1$ or $C_2$ on the sample/reagent tray or from a well 36 to a cuvette 10 at the cuvette access station A on turntable 11. Alternately, pipette 18 can transfer sample diluents (buffers) from the reagent bottles 25 at container access stations $C_3$ or $C_4$ on the sample/reagent tray 15 to a well 36 at a container access station $C_1$ or $C_2$. In addition, it can transfer liquids from one well 36 to another, or from a cup 35 to a well 36 for dilution purposes at container access stations $C_1$ or $C_2$. Direct transfer of reagents from bottles 25 to cuvettes 10 can also take place at cuvette access station A. A wash or pipette alignment procedure can also be periodically accomplished at wash/alignment station D as required. ISE tests are initiated by optional delivery of sample liquids to the ISE station E.

Sample/Reagent Tray

Figure 4:
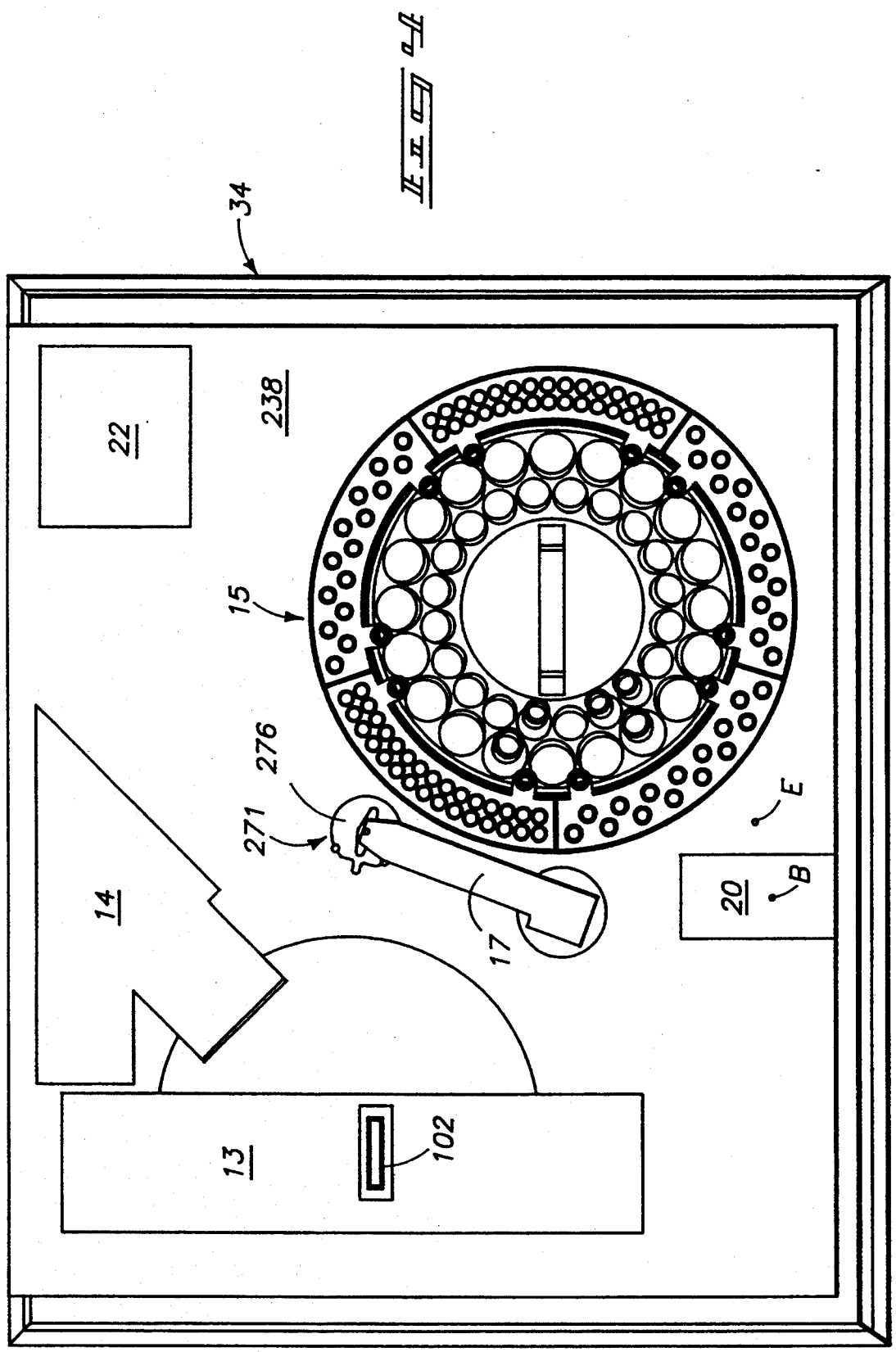
FIG. 4 is a plan view of the chemical instrument enclosure with the cover removed.
Figure 5:
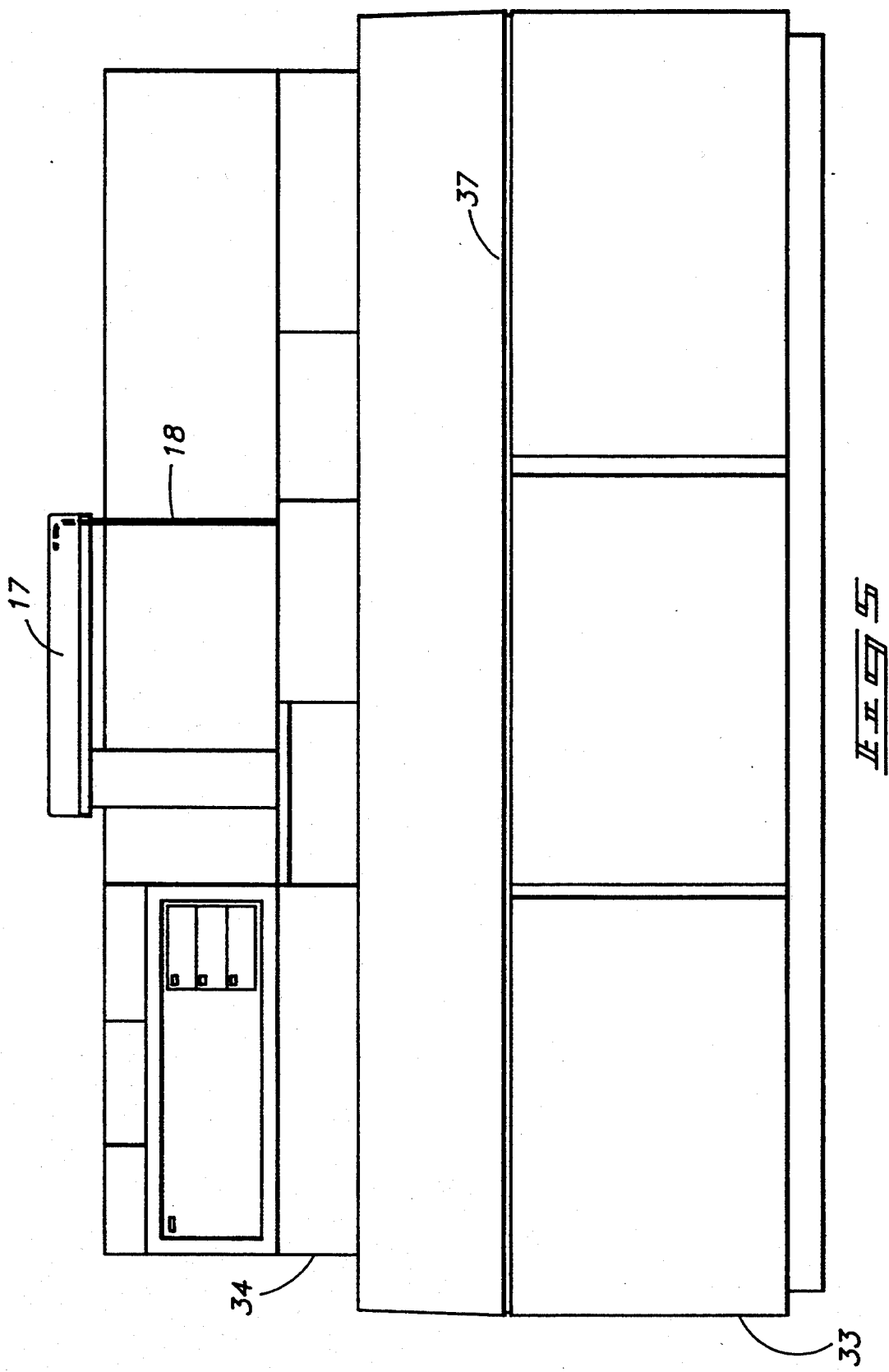
FIG. 5 is a front elevation view of the enclosure.

FIG. 4 illustrates the positional relationship between the sample/reagent tray 15 and the primary components of the chemistry instrument 24 located about the horizontal platform 238 included within the enclosure for the chemistry instrument 24. Details of sample/reagent tray 15 are illustrated in FIGS. 6–9.

Figure 10:
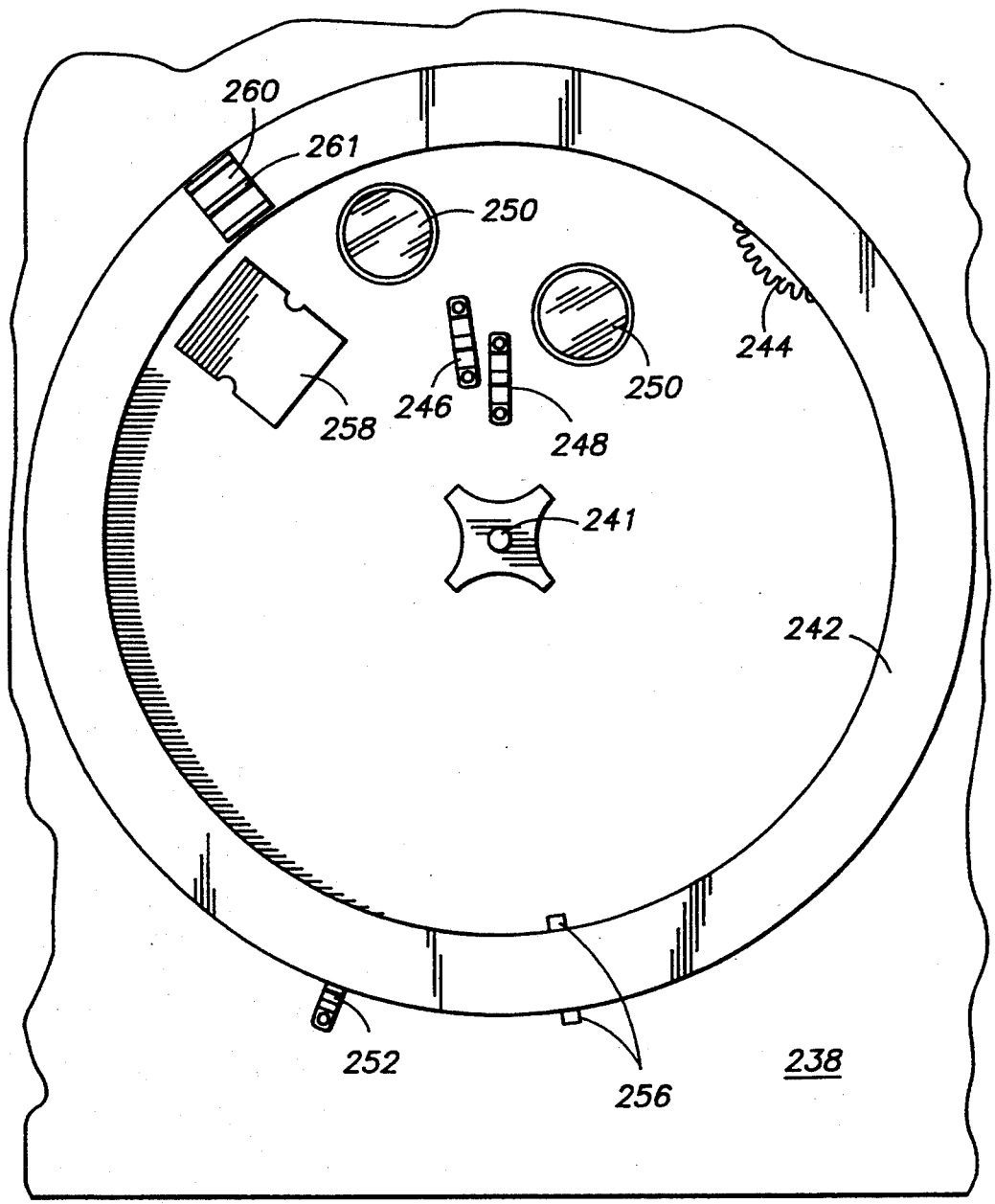
FIG. 10 is a plan view of the supporting platform well.

FIG. 10 illustrates an area of platform 238 forming a recessed well 240 within which the tray 15 is rotatably mounted. Well 240 is centered about a fixed vertical support shaft 241 for the tray 15 and includes a surrounding rim 242. The cross-sectional relationships between these elements is best illustrated in the sectional view shown at FIG. 7.

The illustrated tray 15 is designed to supply reagents to the chemistry instrument 24 from at least two sizes of conventional reagent bottles 25. They are arranged within concentric rings. Additional sizes of bottles can be accommodated within the tray structure by using surrounding adapter sleeves (not shown) that fit properly within receiving tray apertures. Bottle labels read by scanners provide bottle size information and reagent identification data (regent type, lot number and bottle serial number) to the chemistry instrument as needed for monitoring of reagent inventory and life.

The upper end of each reagent bottle 25 is normally covered by a removable threaded cap (not shown) when manually delivered to the chemistry instrument 24. A "peel and stick" protective cover 239, made from a paper or plastic sheet, is utilized across each bottle 25 to prevent contamination and spillage during its usage in the tray 15. Each cover 239 is slit in an intersecting pattern to facilitate passage of pipette 18 through it while accessing reagent liquids.

The cylindrical reagent bottles 25 are tilted from vertical to permit the tip of pipette 18 to penetrate the interior of each bottle to a location adjacent to the lowermost inclined intersection between the container side and bottom walls. This assures more complete removal of liquid from within each reagent bottle 25.

The sample/reagent tray 15 is rotated about its central vertical axis by its engagement with a powered driving gear 244 (FIG. 10) that projects into well 240. Gear 244 meshes with peripheral gear teeth 243 formed about the exterior of tray 15. It is operatively powered by stepper motor 16 (FIG. 1).

The circular tray 15 is rotatably mounted on the framework for the chemistry instrument 24 for rotation about a central vertical axis parallel to the axis of the turntable 11. Tray 15 can be indexed to any desired angular position about its central axis by operation of stepper motor 16.

Figure 6:
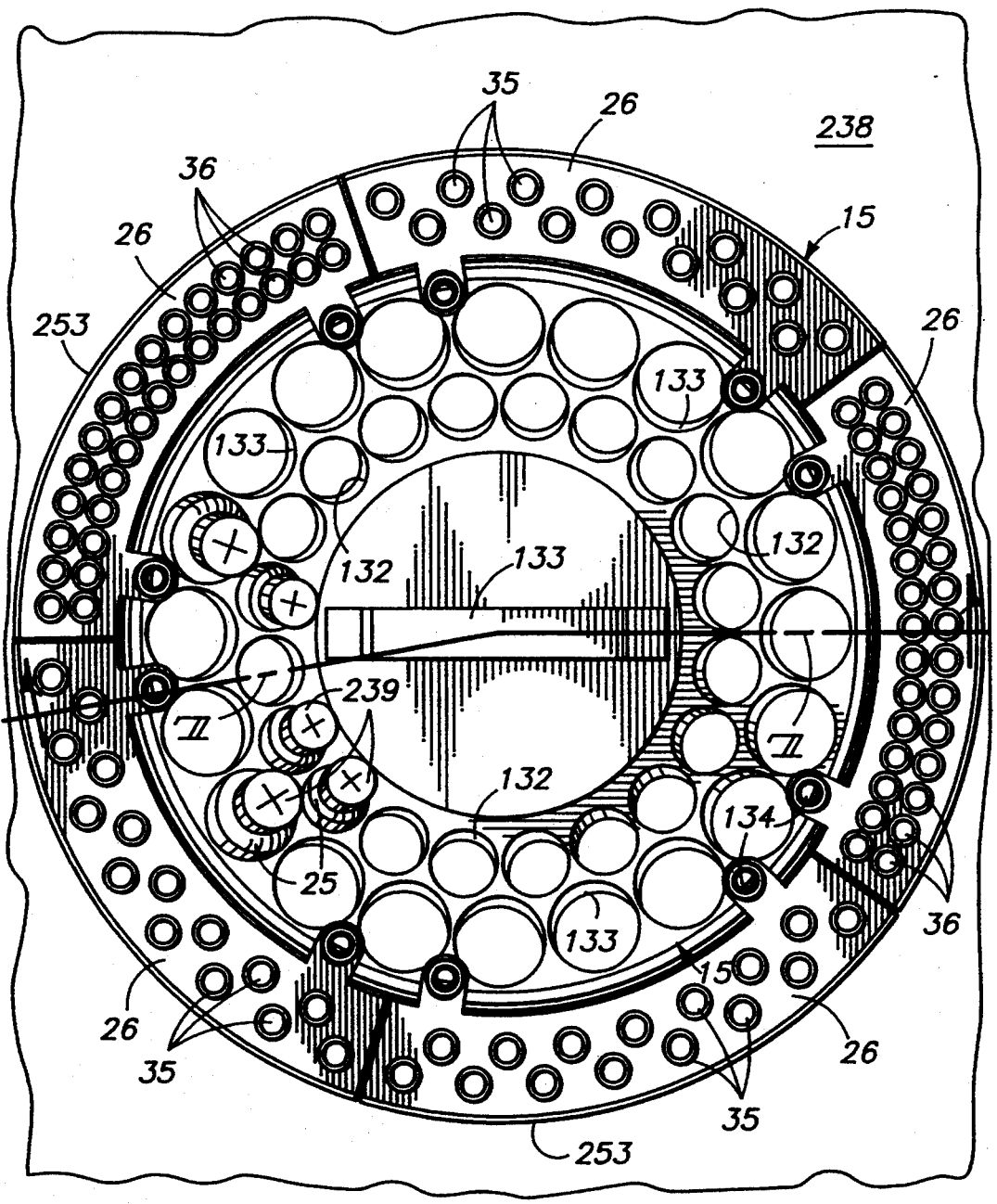
FIG. 6 is a plan view of the assembled sample/reagent tray.

Typical configurations for the open reagent bottles 25 are illustrated in dashed lines in FIG. 7. As seen in FIGS. 6 and 7, the base of tray 15 includes two sets of apertures 132 and 133 suitably sized to receive and support at least two sizes of reagent bottles 25. The apertures also expose the bottom of each bottle 25 for optical viewing of bottom labels applied to the bottles. In a preferred form of a reagent identification system, circular labels having machine-readable indicia printed on their surfaces are scanned from below tray 15 while it is stationary, thus capturing encoded data pertaining to the bottle contents.

Tray 15 includes a central carrying handle 133. Handle 133 facilitates removal of the tray 15 and reagent bottles 25 as a unit, as well as any attached ring segments 26. A plurality of trays 15 can be interchanged in a chemistry instrument 24 as required for specific test purposes. The entire tray 15 can also be removed from the chemistry instrument 24 overnight and during periods of nonuse. It can then be stored in a refrigerated environment or under other conditions as required by the nature of reagents supplied in the tray.

A series of peripheral posts 134 releasably support separable circumferential ring segments 26. The ring segments 26 can be attached to tray 15 while it is located within the chemistry instrument 24 enclosure or at a loading station external to the illustrated equipment.

The individual ring segments 26 shown in FIGS. 6, 7 and 9 are either provided with integral molded wells 36 or removable cups 35. The ring segments 26 are otherwise structurally interchangeable. Each includes radial tabs 135 that fit over the supporting posts 134 when the ring segments 26 are assembled about the tray 15.

To distinguish the two types of ring segments 26, the outer depending flanges 253 on the cup ring segments are notched, as shown by notch 254 in FIG. 9. The nature of a particular ring segment 26 is determined by a light sensor 252 located on platform 238 immediately adjacent to rim 242. The outer upright flanges 253 about the ring segments 26 pass between the elements of the sensor 252. The relative positions of these elements is illustrated in dashed lines in the sectional view shown in FIG. 7.

Both cups 35 and wells 36 have identical interior volumes and shapes, the only physical difference between them being that the cups 35 are separable from a supporting ring segment 26, while the integral wells 36 are not. Cups 35 are less densely arranged about the ring segments 26 so as to provide adequate room about them to facilitate manual handling of the individual cups as needed.

The functions of cups 35 and wells 36 are designed to be complementary to one another. Cups 35 can be added to tray 15 individually or as part of a supporting ring segment 26. Wells 36 are always handled as a group. The portable cups 35 are available only to a human operator for introduction of sample, calibrator, and control liquids. Pipette 18 never delivers liquids to cups 35, but can deliver liquids available within cups 35 to cuvettes 10 in turntable 11 as required for assay purposes. Wells 36 are available only to the chemistry instrument 24. Pipette 18 can use available wells 36 for aliquoting of sample liquid, for dilution of samples before introduction to the ISE module 38, and for mixing of sample liquid with system diluent or a buffer supplied from a bottle 25 on the sample/reagent tray 15.

Figure 2:
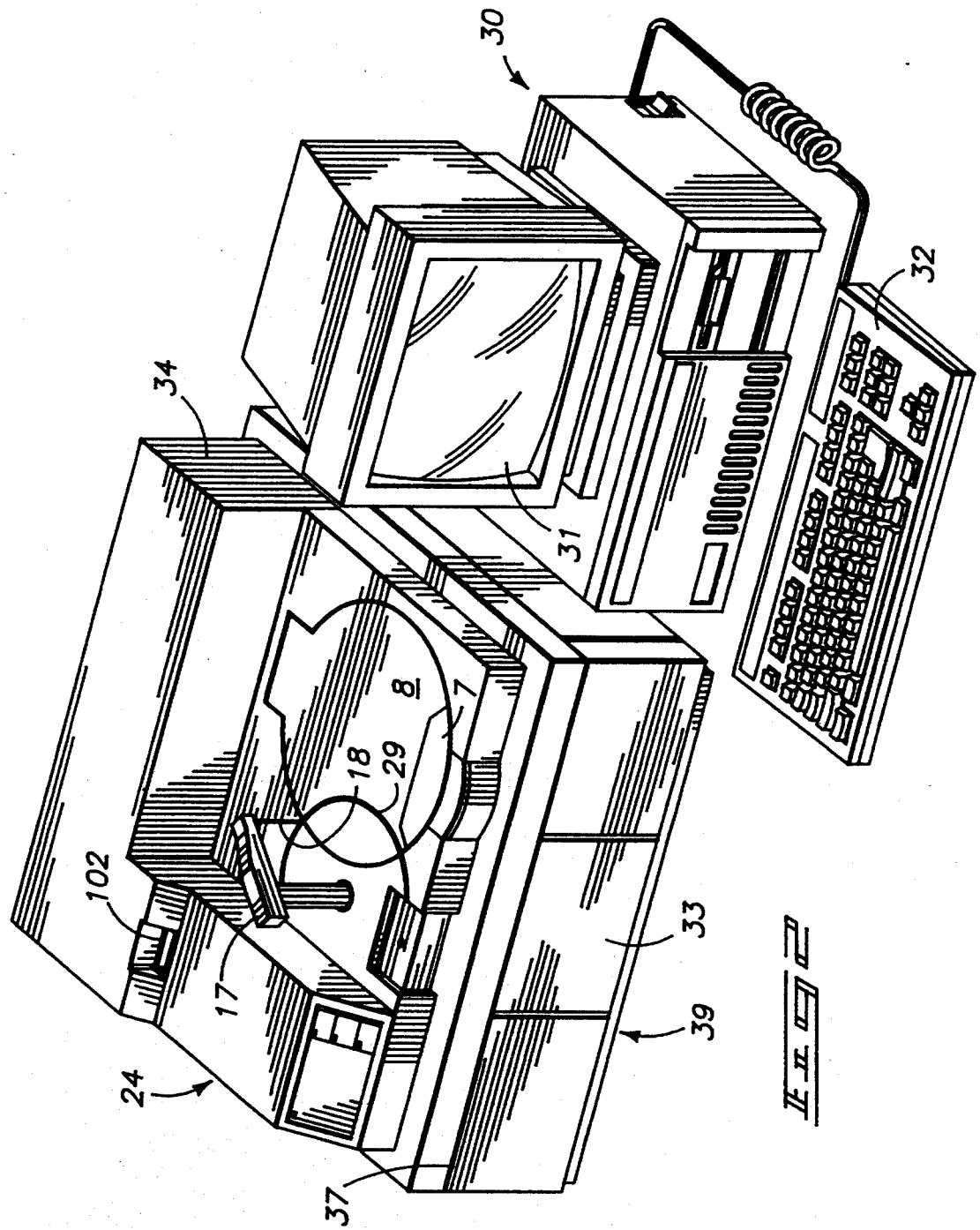
FIG. 2 is a perspective view of the analyzer.

Manual access to the sample/reagent tray 15 is available through the hinged tray access cover 8 shown in FIGS. 2 and 3. Access to the individual ring segments 26 is provided by the segment access port 7. While mechanical interlocks can be provided to restrict opening of cover 8 and port 7, they are not essential. Sensors (not shown) are provided to detect their opening and to alert monitoring software residing in workstation 30 of such events.

Indexing of tray 15 is accomplished by a circular notched indexing ring 245 formed at its underside, which moves between an optical sensor 246 coupled to workstation 30. A reference "home" angular position of tray 15 about the vertical axis of shaft 241 is determined by a projecting index tab 247 at the bottom of tray 15, which is detected by an optical sensor 248 within well 240. The relative positions of these elements is also illustrated in dashed lines in FIG. 7.

A pair of optical scanner ports 250 are located in the base of well 240 directly under the two circular paths of reagent bottles 25 supported by tray 15. Scanning devices under the ports 250 are provided to read encoded end labels attached to each reagent bottle 25. Information on the labels, read through openings under each bottle 25, might relate to reagent identification, lot numbers and reagent aging information.

A line-of-sight optical sensor 256 is arranged across rim 242 for sensing the presence of the removable cups 35 in the ring segments 26. The relative positions of these elements is also illustrated in dashed lines in the sectional view shown in FIG. 7. By combining tray indexing information, segment identification information and cup presence information together with liquid transfer data, workstation 30 can maintain an accurate inventory of the cups 35 and wells 36 available for use with respect to tests being conducted on the chemistry instrument 24.

A conductive metal plate 258 is fixed within well 240 under the circular paths of the reagent bottles 25. The upper surface of plate 258 is spaced from, but in close proximity to, the exposed bottom surfaces of the reagent bottles 25 (FIG. 7). Similarly, a conductive metal plate 260 is fixed across the upper surface of rim 242. It includes ribs 261 in close proximity alongside cups 35 and wells 36 within the ring segments 26. Plate 258 is used for capacitive sensing of liquid level within the reagent bottles 25 as liquid within them is approached by the descending pipette 18. Plate 260 performs the same functions with respect to liquid level sensing within cups 35 and wells 36. The liquid level sensing mechanism including these elements is described below.

Reagent Bottle Identification

Machine-readable identifying information is encoded at the bottom of each reagent bottle 25 upon a printed label 325 detailed in FIGS. 11 and 12. The label can be secured to the circular bottom surface of the reagent bottle 25 by any suitable adhesive system.

Each label 325 preferably has a light surface background on which a contrasting pattern of dots are imprinted. While circular dots are illustrated in FIG. 11, other suitable dot shapes can be used as well.

The label pattern shown in FIG. 11 includes every possible dot location in the present encoding pattern. It is to be understood that the encoded pattern identifying a specific reagent bottle will display a unique arrangement of both dots and blank areas where the dots are now illustrated, the pattern being dependent upon the digital code representative of the encoded data. The code utilized on the labels 325 is a multi-bit binary code representing an identification code for a specific reagent bottle.

Identification label 325 includes a spaced pair of position reference dots 326 and 327 which define and orient a label area. Position reference dot 326 is a central position dot, designating the approximate center of the reagent bottle bottom surface. Position reference dot 327 is an orientation dot which is located radially outward from central position dot 326 to define a label orientation.

The label area is divided into a plurality of bit fields whose positions are defined by position reference dots 326 and 327. Each bit field maps to a single bit of the multi-bit binary bottle identification code. The binary value of each bit of the multi-bit binary identification code is determined by whether a bit dot 328 is present within the mapped bit field.

In general, position reference dots 326 and 327 have a minimum area and the bit dots 328 have a maximum area. The minimum area of position reference dots 326 and 327 is greater than the maximum area of bit dots 328 so that position reference dots 326 and 327 can be easily distinguished from bit dots 328. In the preferred embodiment, position reference dots 326 and 327 have a diameter of about 0.054". Bit dots 328 have a diameter of about 0.034".

The configuration described above produces a pattern of 45 dots that can be effectively imprinted within a label area having a diameter of one half inch. Position reference dot 326 identifies the center of the pattern. Position reference dot 327 is located at the rim of the pattern as an angular index. The label data is encoded by smaller bit dots 328. The bit dots 328 are spaced on approximately 0.1" centers.

The mapping of bit fields to binary code bits is indicated in FIG. 12. The bit dots designated by the digits 0–6 encode seven check bits. The label information is encoded by the bit dots designated by the digits 7–43, with dot 7 being the least significant bit. The forty-three illustrated bit dots 328 provide forty-three bits of binary data, which is sufficient to encode eleven decimal digits.

A conventional Hamming error detection/correction code can be used to encode the label information. Seven check bits are computed from the data bits and form a part of the label pattern. When the label is read, the encoding of the check bits allows the detection and correction of an error in any one of the bit locations about the label 325. Any single bit may be in error, but the encoded information on the label 325 can still be recognized correctly. If errors exist at any two bit locations, the existence of an error will be detected, but the information on the label cannot be decoded. If errors exist in more than two bits, the resulting information will be unpredictable.

The equipment for reading information encoded on labels 325 is diagrammatically illustrated in FIG. 13. Each reagent bottle 25 is held within the sample/reagent tray 15 at a location above the horizontal surface of well 240. Each label 325 can be indexed over one of the optical scanner ports 250 for label reading purposes. The optical scanner ports 250 each include a circular filter 330 that blocks entrance of room light while permitting passage of illuminating light directed to the label 325 from a location under the port 250.

The information encoded on labels 325 is read by a camera 332 in response to reflected light provided by a circumferential ring of light emitting diodes 334 directed toward the bottom surface of a reagent bottle 25. Camera 332, which is essentially a video camera, includes a lens system 335 positioned behind the ring of diodes 334. Lens system 335 focuses light from the bottom of reagent bottle 25 onto a receiving scanning matrix 336 of image sensors. In the illustrated example, the matrix 336 has a 192×165 pixel area capable of discriminating between the above-identified dot array.

The camera 132 conveys digital information to controller 312 from which a digitized image of the bottom of each reagent bottle 25 can be stored in memory. This image can then be electronically "rotated" about the center dot 326 and indexed relative to the rim dot 327 to orient bit dots 328 for electronic analysis. The electronic functions required in such an analysis are believed to be well-known in image-analyzing technology today. No further details are necessary in order to enable those skilled in this area of technology to construct and successfully use the described scanning apparatus and associated labels.

The unique labeling scheme described above allows for simple and quick decoding of reagent bottle identification data. Once the label has been oriented properly and broken into bit fields, only the presence or absence of a dot in that bit field need be determined. This is in contrast to many other types of labeling schemes in which indicia size or spacing is variable to represent coded information. In the scheme of this invention, all bit dot sizes and all spacing between bit dots remain constant, making for much simpler detection and decoding. Simple thresholding can be used within each bit field to detect whether a dot is present of sufficient area to constitute a bit dot.

Reagent Monitoring

Overview

The purpose of reagent monitoring is to warn the operator when a reagent within a particular bottle 25 has been in use too long. Where two chemistry instruments 24 are used in tandem with a common workstation 30, each instrument tracks the age and volume of one working bottle for each reagent defined in its data base. The age of the working bottle is maintained in the memory of the instrument 24 even when it is removed from it for overnight storage of other purposes.

This description pertains to the manner by which the chemistry instrument 24 manages the sample/reagent tray 15. It describes the way in which the working bottles 25 of reagent and the working lifetimes of their reagent contents are tracked, how the instrument decides when a new bottle is to be used, and how reagent lot number changes are handled. It describes how the system reacts when the tray access cover 8 is opened. It further describes the activities of the system when a reagent bottle 25 is found to contain less reagent than is required for a requisitioned assay.

The chemistry instrument 24 shown in the drawings includes a sample/reagent tray 15 having room for forty reagent bottles 25. As one example, these might be twenty large (30 ml) bottles and twenty small (12 ml) ones. The tray 15 can be accessed by manually opening the hinged tray access cover 8. Cover 8 is provided with a sensor so that the controller system will be provided with a signal indicating whenever the reagent bottles 25 might have been disturbed.

Sample/reagent tray controller 312 will operate the motor 16 and the electronics associated with optical scanner ports 250 to read the labels at the bottom of every reagent bottle 25 at the conclusion of any operation requiring tray access cover 8 to have been opened. This information is used by the software to update stored data pertaining to their reagent identifications, lot codes, and serial numbers.

The volume in each reagent bottle 25 accessed by pipette 18 is measured each time that the instrument uses a reagent. This is done by using the pipette's fluid sensing capability to detect the elevation of liquid, which is then related to the interior volume of the bottle by using stored information relating to the bottle size.

The logic system associated with sample/reagent tray 15 supports a mode of operation wherein two bottles 25 of each reagent can be on the tray 15 at any given time. When the working bottle 25 is emptied, the instrument 24 will then start loading from the reserve bottle.

Any secondary or non-working bottles of reagents are also timed while in the tray 15. However, since they are not in use, their respective liquid volumes are not tracked. They are tracked by their positions within tray 15 only. Their age is not maintained in the instrument's memory if they are removed. It is possible to remove the tray 15 after the instrument 24 has been turned off and subsequently replace it before powering up the instrument 24 again. In this case, all of the bottles's ages will be maintained in memory.

Once introduced into the chemistry instrument 24, the contents of a primary reagent bottle 25 will continue to be used by it until the bottle is empty or is removed by an operator. When a bottle 25 containing reagent is first introduced into the chemistry instrument 24 in the tray 15, the controlling logic will assume it to be freshly reconstituted. A working expiration time will be established for it at such introduction. The number of hours remaining before expiration is available for display as needed on the monitor 31. If a reagent bottle 25 remains in the system beyond this time, the operator will be warned by an appropriate display message and the contents of the bottle will be "marked" as being expired on a status screen.

Reagent Definition Data Base

A reagent definition data base resides in disk memory provided with workstation 30 in the form of a shared data file (information common to two chemistry instruments 24) and one or more instrument-specific data files.

The shared data file defines the characteristics of each reagent. This includes the name, bottle identification, fluid type and working lifetime. The data pertaining to working lifetime is set up by the operator. The working lifetime is defined as the length of time during which the reagent within a bottle 25 is considered functionally usable from the time a new bottle is opened or reconstituted. The bottle identification is a number encoded into a machine-readable bottle label. The identification data captured by the bottle label scanning equipment also encodes the size and shape of the bottles. Ranges of identification values are reserved for particular bottle types. Captured information pertaining to fluid type is used by the operator interface in workstation 30 to generate appropriate choice lists.

The instrument-specific data base stores the status of each working reagent bottle 25, including working lot number, serial number, expiration time and volume. This data is stored in a non-volatile fashion so as to maintain data concerning each working reagent bottle even when it has been removed from the system or during periods when power has been lost. The volume remaining in each working reagent bottle is updated each time the bottle is used.

Sample/Reagent Tray Status Data

Each instrument CPU board maintains the data pertaining to the status of the bottles 25 in each tray position in non-volatile random access memory. For each position in the tray, the system stores the type of reagent as well as its lot code and serial number, plus the volume, working expiration time and status of the container in question. A special software flag is set when the tray access cover 8 is opened or after power interruption, and cleared when the label on each bottle 25 within tray 15 is subsequently read by the scanning devices under optical scanner ports 250. When it is set, the prior data concerning the bottles is not totally invalid, since it represents the state of the bottle before the event.

Data is maintained in the instrument 24 as to whether or not each reagent is required by waiting, on-hold and active instrument workload. This is maintained by a background status update task in the instrument CPU board, so that it is continually updated. This data is used by the reagent status screen to show which reagents are required by the workload. This can also be used by an operator to do requirements checking through workstation 30 to warn for insufficient reagent.

Fluid Transfers From Reagent Bottles

Fluid transfers involving reagent bottles 25 are always done from working or primary bottles of a reagent. The working bottle is recognized by its label information. The system supports having multiple bottles of each reagent, one designated by the instrument as a working bottle and the others as reserve bottles. When the working bottle becomes empty a reserve bottle becomes the new working bottle.

Proper operation of the chemistry instrument 24 does not permit liquid to be added to a working bottle. A bottle will be rejected if its liquid volume has increased above a specified minimum amount since it was last accessed by probe 18. It is assumed that an operator might open the cover, pour some of the working reagent from a particular reagent bottle 25, and then return the reagent bottle to sample/reagent tray 15. Such activity can be accommodated by the controlling software, since it is presumed that removal of liquid from a reagent bottle 25 will not contaminate its content, whereas addition of liquid to it will.

Every time a liquid transfer is to be made from a bottle 25, the working bottle must be identified or selected from a set of reserve bottles. When the transfer is started, a liquid transfer module controller is provided with data containing limits within which the volume in the appropriate working bottle should be found. If the liquid transfer module controller finds the volume within the identified reagent bottle 25 to be short or outside the limits, it aborts the transfer, discards any received liquid in the pipette 18 and communicates data relating to the measured volume to the instrument CPU board.

If no working bottle for a needed reagent can be identified by the software, a new working bottle must be selected. The reserve bottles of reagent are each marked in memory with a time of appearance on the tray 15. The oldest reserve bottle then becomes the next working bottle. If more than one reserve bottle is marked in memory with the same time of appearance, the one with the lowest numbered tray position will be arbitrarily selected.

The above rules are only followed for the lot number currently in use. If more than one lot of reagent is present, the working reagent bottle 25 will be chosen from the bottles of the working lot number. All bottles of other lots are considered reserve bottles.

The capacitive sensing system for detecting fluid levels within the instrument 24 is utilized to capture reagent volume information for each working bottle of reagent on a real-time basis during all operations. As pipette 18 is lowered into a reagent bottle 25, it is stopped by operation of the liquid transfer module controller when the liquid surface within the bottle is sensed. The liquid transfer module controller has data relating to the bottle identification, which implies the bottle's diameter and dead volume. The volume of reagent within the bottle 25 is then deduced by the liquid transfer module controller from the height of the pipette tip.

Each time a reagent bottle 25 is probed by pipette 18, the stored data relating to the volume of reagent remaining within it is verified and updated, if necessary. The liquid transfer module controller communicates data with respect to the volume of reagent in the reagent bottle 25 back to the instrument CPU board in microliters, excluding the dead volume. If a transfer was performed from the reagent bottle 25, the reported volume is corrected for the volume of reagent removed.

The instrument CPU board is also programmed to respond to unexpected volumes of reagent measured by the probing action of pipette 18. When a fluid transfer from a reagent bottle 25 is performed, the liquid transfer module controller calculates the high and low limits to the acceptable volume that should be within the selected bottle. The software allows for a predetermined volume measurement error tolerance. If the tray access cover 8 has not been opened since the last time that the selected bottle 25 was probed, the volume of reagent within it should not deviate from the last-measured volume by more than the tolerance in either direction. If it does, this is reported as a warning to the operator. The operator's normal course of action in this case is to go to diagnostics.

If the tray access cover 8 has been opened since the last time the selected working reagent bottle 25 was probed, the instrument 24 will expect the volume of reagent within each reagent bottle 25 to be between the last volume (plus tolerance) and zero. If the measured volume of reagent within a probed bottle 25 is found to be too great, use of the bottle is not allowed. This guards against use of bottle contents that might have been accidently or purposefully contaminated or diluted during their use in the instrument.

The instrument 24 is programmed to respond to data indicating that the volume of reagent in a working bottle is short of that required for a requisitioned assay or test. Each time that such a reagent bottle 25 is probed, the liquid transfer module controller will report that its liquid content is empty. This is reported to the operator by a message on monitor 31.

If a reagent bottle 25 is found short during a fluid transfer, the contents of the probe are discarded, and the run being loaded is canceled. If other reagent bottles 25 of this type are on the tray, a new working bottle is selected and the run is rescheduled. Otherwise, the run is put on hold.

When the instrument CPU board is re-initialized, it assumes that power has been removed from the chemistry instrument 24. Since the tray access cover 8 might have been opened while power was removed, the system behaves as if the cover 8 has been opened. The instrument CPU board is capable of continuing to monitor the sensors that detect opening of cover 8 while carrying out diagnostic procedures, so the tray 15 is only scanned as necessary after diagnostics.

Every time the cover 8 has been opened, each reagent bottle 25 is marked in the controlling software as requiring reading of its label. This causes the bottle label to be read. When the cover 8 is again closed, the system scans the sample/reagent tray 15 to read all the bottle labels. The system remembers the tray status in memory until the new status is figured out completely. Thus, if the system is reset during a scan, the previous data is not lost. If power is lost while a new status is being written, the system starts a new scan.

When a reagent bottle 25 is recognized as a new working bottle, the working bottle expiration time is updated in the reagent data base. If a test uses an external reagent blank, a new blank value is stored when a new bottle is started for any reagent involved in the test's load sequence. The scheduling software within the instrument CPU board will then load an external reagent blank cuvette for the first run of turntable 11 scheduled using the new reagent bottle 25.

If a patient or quality control test run is being loaded onto the turntable 11 and an external reagent blank has been loaded from a working reagent bottle, but a new bottle is started before the reaction cuvette for the test has been loaded, the test run must be rescheduled by the controlling software. Both the external reagent blank and the reaction cuvette must be loaded using reagent from the same reagent bottle 25.

Bottles 25 containing reagent of a lot other than the working lot are ignored until the system has no choice but to pick a new working reagent from them. A new working reagent is then selected from them by using the oldest appearance time or the lowest tray position, if the times are equal.

The system requires a test to be calibrated before running a patient or quality control test from a new lot. When a new working reagent must be selected, and all of the choices are from a new lot, the test is marked as requiring calibration. If a calibration request is waiting, a working bottle is selected and the calibration is scheduled.

The invention has been described in language more or less specific as to structural features. It is to be understood, however, that the invention is not limited to the specific features shown, since the means and construction herein disclosed comprise a preferred form of putting the invention into effect. The invention is, therefore, claimed in any of its forms or modifications within the proper scope of the appended claims appropriately interpreted to include appropriate equivalents.

We claim:

1. A method of identifying a labeled reagent bottle having a bottle identification code in the form of a multi-bit binary code imprinted on its bottom surface within a label area having a surface background on which a contrasting pattern of dots is imprinted;
   the pattern of dots including a spaced pair of imprinted position reference dots;
   the remaining label area being divided into a plurality of bit fields;
   the method comprising the following steps:
   (a) detecting the locations of a spaced pair of position reference dots in the form of a central position dot located at the approximate center of an imprinted pattern on the bottom surface of a reagent bottle and an orientation dot spaced radially outward from the central position dot at the rim of the pattern, the central position dot and orientation dot defining and orienting a label area containing both of them;
   (b) dividing the label area into a plurality of bit fields having bit dots imprinted in selected bit fields about the label area wherein each bit field maps to a single bit of a multi-bit binary code and the binary value of each bit of the multi-bit binary code determines whether a bit dot is present in the mapped bit field, the bit fields surrounding the central position dot and being defined by the spaced pair of position reference dots, the spacing between the imprinted pair of reference dots being substantially greater than the spacing between adjacent bit fields about the label area and also being greater than the spacing between each of the imprinted reference dots and the bit fields adjacent to it;
   (c) detecting whether a bit dot is present within each bit field;
   (d) distinguishing the imprinted position reference dots from the imprinted bit dots by their relatively greater areas and spacing, the imprinted position reference dots having a minimum area and the imprinted bit dots having a maximum area, the minimum area of the imprinted position reference dots being greater than the maximum area of the imprinted bit dots; and (e) mapping each bit field to a single bit of the multi-bit binary code to determine the binary value of each bit of the multi-bit binary code.

2. The method of claim 1, wherein the multi-bit binary code includes a plurality of check bits.

3. The method of claim 1, wherein the multi-bit binary code specifies the reagent bottle size, its serial number, and the identification of a reagent within the bottle.

4. The method of claim 1, wherein the detecting step (a) is carried out by:
focusing an image sensor on the bottom surface of a reagent bottle; and
directing a ring of light-emitting diodes toward the bottom surface of the reagent bottle, the light-emitting diodes being arranged about the image sensor.

5. The method of claim 1, wherein method steps (a) through (e) are preceded by the following steps:
(f) placing reagent bottles within a reagent tray having a plurality of tray apertures therein which receive a plurality of coded reagent bottles and which expose the bottom surface of each bottle for optical viewing of its bottle identification code; and
(g) indexing a selected tray aperture over an optical scanner positioned below the reagent tray for reading the identification code on the bottom surface of a reagent bottle through the selected tray aperture.

6. The method of claim 5, further comprising the following step:
(h) monitoring the locations of individual reagent bottles within the reagent tray.

7. The method of claim 5, further comprising the following steps:
(h) monitoring the locations of individual reagent bottles within the reagent tray;
(i) determining the age of reagent within each reagent bottle from information encoded within the multi-bit binary code; and
(j) calculating the volume of reagent remaining within each reagent bottle.

8. The method of claim 5, further comprising the following steps:
(h) monitoring the locations of individual reagent bottles within the reagent tray;
(i) determining the age of reagent within each reagent bottle from information encoded within the multi-bit binary code;
(j) calculating the volume of reagent remaining within each reagent bottle; and
(k) prompting an operator upon expiration of the contents of a reagent bottle.

9. The method of claim 5, further comprising the following steps:
(h) storing digital information with respect to a bottle identification code determined in step (e) for each reagent bottle, the location of each reagent bottle within the reagent tray, and reagent status for each reagent bottle;
(i) monitoring the locations of individual reagent bottles within the reagent tray;
(j) determining the age of reagent within each reagent bottle from information encoded within the multi-bit binary code;
(k) calculating the volume of reagent remaining within each reagent bottle; and
(l) prompting an operator upon expiration of the contents of a reagent bottle.

10. The method of claim 5, further comprising the following steps:
(h) storing digital information with respect to a bottle identification code determined in step (e) for each reagent bottle, the location of each reagent bottle within the reagent tray, and reagent status for each reagent bottle;
(i) measuring the actual volume of reagent within a reagent bottle; and
(j) prompting an operator upon expiration of the contents of a reagent bottle.

* * * * *